US010314503B2

(12) United States Patent
Prerau et al.

(10) Patent No.: US 10,314,503 B2
(45) Date of Patent: Jun. 11, 2019

(54) SYSTEMS AND METHODS FOR TRACKING NON-STATIONARY SPECTRAL STRUCTURE AND DYNAMICS IN PHYSIOLOGICAL DATA

(71) Applicants: Michael J. Prerau, Somerville, MA (US); Patrick L. Purdon, Somerville, MA (US); Uri Eden, Somerville, MA (US)

(72) Inventors: Michael J. Prerau, Somerville, MA (US); Patrick L. Purdon, Somerville, MA (US); Uri Eden, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 456 days.

(21) Appl. No.: 14/900,805

(22) PCT Filed: Jun. 27, 2014

(86) PCT No.: PCT/US2014/044720
§ 371 (c)(1),
(2) Date: Dec. 22, 2015

(87) PCT Pub. No.: WO2014/210549
PCT Pub. Date: Dec. 31, 2014

(65) Prior Publication Data
US 2016/0150988 A1    Jun. 2, 2016

Related U.S. Application Data
(60) Provisional application No. 61/840,093, filed on Jun. 27, 2013.

(51) Int. Cl.
*A61B 5/00*    (2006.01)
*A61B 5/04*    (2006.01)
(Continued)

(52) U.S. Cl.
CPC .......... *A61B 5/04012* (2013.01); *A61B 5/048* (2013.01); *A61B 5/4806* (2013.01);
(Continued)

(58) Field of Classification Search
CPC ..... A61B 5/04012; A61B 5/725; A61B 5/048; A61B 5/4806; A61B 5/4839;
(Continued)

(56) References Cited

U.S. PATENT DOCUMENTS 2,507,631 A    5/1950    Hartmann et al.
2,957,880 A    10/1960    Rometsch
(Continued)

FOREIGN PATENT DOCUMENTS

EP    0765630 A1    4/1997
JP    2005339533 A    12/2005
(Continued)

OTHER PUBLICATIONS

Sartori, et al., On-Line Estimation of Propofol Pharmacodynamic Parameters, Proceedings of the 2005 IEEE Engineering in Medicine and Biology 27th Annual Conference, 2005, pp. 74-77.
(Continued)

*Primary Examiner* — Tiffany Weston
*Assistant Examiner* — Tho Q Tran
(74) *Attorney, Agent, or Firm* — Quarles & Brady LLP

(57) ABSTRACT

Systems and methods for tracking dynamic structure in physiological data are provided. In some aspects, the method includes providing physiological data, including electroencephalogram ("EEG") data, acquired from a subject and assembling a time-frequency representation of signals from the physiological data. The method also includes generating a dynamic model of at least one non-stationary spectral feature, such as at least one non-stationary spectral peak, using the time-frequency representation and a user indica-
(Continued)

tion, and applying a dynamic model of at least one non-stationary spectral feature in a parameter estimation algorithm to compute concurrent estimates of spectral parameters describing the at least one non-stationary spectral feature. The method also includes tracking the spectral parameters of the at least one spectral feature over time.

35 Claims, 6 Drawing Sheets

(51) Int. Cl.
    *A61B 5/048*     (2006.01)
    *A61B 5/0402*     (2006.01)
    *A61B 5/0488*     (2006.01)
    *A61B 5/0496*     (2006.01)
    *A61B 5/053*     (2006.01)

(52) U.S. Cl.
    CPC ............ *A61B 5/725* (2013.01); *A61B 5/0402* (2013.01); *A61B 5/0488* (2013.01); *A61B 5/0496* (2013.01); *A61B 5/0533* (2013.01); *A61B 5/4821* (2013.01); *A61B 5/4839* (2013.01); *A61B 5/7253* (2013.01)

(58) Field of Classification Search
    CPC ... A61B 5/7253; A61B 5/0496; A61B 5/0488; A61B 5/4821; A61B 5/0402; A61B 5/0533
    See application file for complete search history.

(56) References Cited

U.S. PATENT DOCUMENTS

| | | | |
|---|---|---|---|
| 4,195,643 A | | 4/1980 | Pratt, Jr. |
| 4,392,849 A | | 7/1983 | Petre et al. |
| 4,448,199 A | | 5/1984 | Schmid |
| 4,755,795 A | * | 7/1988 | Page .................. G01R 23/165 341/122 |
| 4,911,167 A | | 3/1990 | Corenman et al. |
| 5,195,530 A | | 3/1993 | Shindel |
| 5,845,241 A | * | 12/1998 | Owechko ............... G10L 25/48 704/203 |
| 5,851,438 A | | 12/1998 | Chan |
| 5,908,850 A | | 6/1999 | Zeitlin et al. |
| 6,025,362 A | | 2/2000 | Fukunaga et al. |
| 6,032,063 A | | 2/2000 | Hoar et al. |
| 6,032,065 A | | 2/2000 | Brown |
| 6,067,467 A | | 5/2000 | John |
| 6,281,242 B1 | | 8/2001 | Regan et al. |
| 6,338,713 B1 | | 1/2002 | Chamoun et al. |
| 6,708,051 B1 | | 3/2004 | Durousseau |
| 6,740,214 B1 | | 5/2004 | Dobson et al. |
| 6,944,565 B2 | | 9/2005 | Meneilage et al. |
| 7,006,872 B2 | | 2/2006 | Gielen et al. |
| 7,286,871 B2 | | 10/2007 | Cohen |
| 7,462,151 B2 | * | 12/2008 | Childre .................. A61B 5/024 600/300 |
| 7,783,343 B2 | | 8/2010 | Sarkela et al. |
| 8,025,404 B2 | | 9/2011 | Bolger et al. |
| 8,073,534 B2 | | 12/2011 | Low |
| 8,244,526 B2 | | 8/2012 | Vos et al. |
| 8,298,154 B2 | | 10/2012 | Hete et al. |
| 8,315,970 B2 | | 11/2012 | Zalay et al. |
| 8,521,294 B2 | | 8/2013 | Sarma et al. |
| 8,630,722 B2 | | 1/2014 | Condurso et al. |
| 2002/0128798 A1 | | 9/2002 | Lange et al. |
| 2002/0156357 A1 | | 10/2002 | Axelgaard |
| 2003/0088167 A1 | | 5/2003 | Fendrock et al. |
| 2003/0130585 A1 | | 7/2003 | Wenger |
| 2004/0143021 A1 | | 7/2004 | Larijani |
| 2004/0193068 A1 | | 9/2004 | Burton et al. |
| 2004/0204880 A1 | * | 10/2004 | Cheriet ................ H04B 17/309 702/77 |
| 2005/0054941 A1 | | 3/2005 | Ting et al. |
| 2005/0256415 A1 | | 11/2005 | Tan et al. |
| 2006/0135880 A1 | | 6/2006 | Sarkela |
| 2006/0178585 A1 | | 8/2006 | Sharrock |
| 2006/0229519 A1 | | 10/2006 | Fujiwara et al. |
| 2007/0067003 A1 | | 3/2007 | Sanchez et al. |
| 2007/0073355 A1 | | 3/2007 | Dilorenzo |
| 2007/0100389 A1 | | 5/2007 | Jaax et al. |
| 2007/0123468 A1 | | 5/2007 | Jenkins |
| 2007/0150025 A1 | | 6/2007 | Dilorenzo et al. |
| 2007/0167694 A1 | | 7/2007 | Causevic et al. |
| 2007/0191704 A1 | | 8/2007 | DeCharms |
| 2007/0203540 A1 | | 8/2007 | Goetz et al. |
| 2008/0021345 A1 | | 1/2008 | Kern et al. |
| 2008/0249431 A1 | | 10/2008 | Bier et al. |
| 2008/0306397 A1 | | 12/2008 | Bonmassar et al. |
| 2010/0023089 A1 | | 1/2010 | DiLorenzo |
| 2010/0280333 A1 | | 11/2010 | Parshuram et al. |
| 2011/0044524 A1 | | 2/2011 | Wang et al. |
| 2011/0082381 A1 | | 4/2011 | Uthman et al. |
| 2011/0125046 A1 | | 5/2011 | Burton et al. |
| 2011/0137134 A1 | | 6/2011 | Hemmerling et al. |
| 2011/0137297 A1 | | 6/2011 | Kiani et al. |
| 2011/0218454 A1 | | 9/2011 | Low |
| 2011/0224570 A1 | | 9/2011 | Causevic |
| 2012/0022391 A1 | | 1/2012 | Leuthardt |
| 2012/0029378 A1 | | 2/2012 | Low |
| 2012/0101401 A1 | * | 4/2012 | Faul .................... A61B 5/0476 600/544 |
| 2012/0250963 A1 | | 10/2012 | Carroll et al. |
| 2013/0131464 A1 | | 5/2013 | Westbrook et al. |
| 2013/0197339 A1 | | 8/2013 | Bardakjian et al. |
| 2013/0211224 A1 | | 8/2013 | Isenhart et al. |
| 2013/0310422 A1 | | 11/2013 | Brown et al. |
| 2013/0331660 A1 | | 12/2013 | Al-Ali et al. |
| 2014/0012100 A1 | | 1/2014 | Al-Ali et al. |
| 2014/0180160 A1 | | 6/2014 | Brown et al. |
| 2014/0187973 A1 | | 7/2014 | Brown et al. |
| 2014/0316217 A1 | | 10/2014 | Purdon et al. |
| 2014/0316218 A1 | | 10/2014 | Purdon et al. |
| 2014/0323897 A1 | | 10/2014 | Brown et al. |
| 2014/0323898 A1 | | 10/2014 | Purdon et al. |
| 2014/0371548 A1 | | 12/2014 | Al-Ali et al. |
| 2015/0011907 A1 | | 1/2015 | Purdon et al. |
| 2015/0080754 A1 | | 3/2015 | Purdon et al. |

FOREIGN PATENT DOCUMENTS

| | | |
|---|---|---|
| JP | 2008178546 A | 8/2008 |
| JP | 2011064558 A | 3/2011 |
| RU | 95243 U1 | 6/2010 |
| WO | 2004036379 A2 | 4/2004 |
| WO | 2004037114 A2 | 5/2004 |
| WO | 2004047632 A1 | 6/2004 |
| WO | 2011160222 A1 | 12/2011 |
| WO | 2012145285 A1 | 10/2012 |
| WO | 2012154701 A1 | 11/2012 |

OTHER PUBLICATIONS

Sawaguchi, et al., A Model-Predictive Hypnosis Control System Under Total Intravenous Anaesthesia, IEEE Transactions on Biomedical Engineering, 2008, 55(3):874-887.

Schaffer, et al., The Effect of the Atmosphere and the Role of Pore Filling on the Sintering of Aluminum, Acta Materialia, 2006, 54(1):131-138.

Schwilden, et al., Closed-Loop Feedback Control of Methohexital Anesthesia by Quantitative EEG Analysis in Humans, Anesthesiology, 1987, 67:341-347.

Schwilden, et al., Closed-Loop Feedback Control of Propofol Anaesthesia by Quantitative EEG Analysis in Humans, Br. J. Anaesth., 1989, 62:290-296.

Struys, et al., Comparison of Closed-Loop Controlled Administration of Propofol Using Bispectral Index as the Controlled Variable Versus "Standard Practice" Controlled Administration, Anesthesiology, 2001, 95(1):6-17.

(56) References Cited

OTHER PUBLICATIONS

Struys, et al., Closed Loops in Anaesthesia, Best Practice & Research Clinical Anaesthesiology, 2006, 20 (1):211-220.
Tan, et al., Sparse Learning via Iterative Minimization With Application to MIMO Radar Imaging, IEEE Transactions on Signal Processing, 2011, 59(3)1088-1101.
Truccolo, et al., A Point Process Framework for Relating Neural Spiking Activity to Spiking History, Neural Ensemble, and Extrinsic Covariate Effects, J. Neurophysiol., 2005, 93:1074-1089.
Van Vugt, Comparison of Spectral Analysis Methods for Characterizing Brain Oscillations, J. Neurosci. Methods, 2007, 162(1-2):49-63.
Vijn, et al., I.v. Anaesthesia and EEG Burst Suppression in Rats: Bolus Injections and Closed-Loop Infusions, British Journal of Anaesthesia, 1998, 81:415-421.
Vusanovic, et al., Microsegregation Phenomena in Al—Cu—Mg Alloy with Considering of Diffusion Phenomena in Primary Phase, Facta Universitatis, Series: Mechanical Engineering, 2001, 1(8):965-980.
Wang, et al., Precipitates and Intermetallic Phases in Precipitation and Hardening Al—Cu—Mg—(Li) Based Alloys, International Materials Reviews, 2005, 50(4):193-215.
Zdunek, et al., Improved M-FOCUSS Algorithm With Overlapping Blocks for Locally Smooth Sparse Signals, IEEE Transactions on Signal Processing, 2008, 56(10):4752-4761.
Article: "Polyesters", http://web.archive.org/web/20020812093256/http://pslc.ws/macrog/pet.htm, Copyright 1995, 1996 Department of Polymer Science, University of Southern Mississippi, 4 pages.
European Patent Office, Extended European Search Report, Application No. 12781958.9, dated Sep. 15, 2014, 12 pages.
PCT International Search Report and Written Opinion, PCT/US2005/042401, dated Jun. 14, 2006, 17 pages.
PCT International Search Report and Written Opinion, PCT/US2009/062072, dated May 12, 2010, 13 pages.
PCT International Search Report and Written Opinion, PCT/US2011/050213, dated May 1, 2012, 12 pages.
PCT International Search Report and Written Opinion, PCT/US2012/036854, dated Aug. 16, 2012, 6 pages.
PCT International Search Report and Written Opinion, PCT/US2013/064852, dated Jan. 23, 2014, 6 pages.
PCT International Search Report and Written Opinion, PCT/US2014/033619, dated Sep. 23, 2014, 12 pages.
PCT International Search Report and Written Opinion, PCT/US2014/035166, dated Aug. 29, 2014, 17 pages.
PCT International Search Report and Written Opinion, PCT/US2014/035178, dated Sep. 15, 2014, 15 pages.
PCT International Search Report and Written Opinion, PCT/US2014/035319, dated Sep. 26, 2014, 15 pages.
PCT International Search Report and Written Opinion, PCT/US2014/035329, dated Sep. 26, 2014, 11 pages.
PCT International Search Report and Written Opinion, PCT/US2014/035333, dated Sep. 26, 2014, 14 pages.
PCT International Search Report and Written Opinion, PCT/US2014/044692, dated Nov. 4, 2014, 12 pages.
PCT International Search Report and Written Opinion, PCT/US2014/044720, dated Nov. 28, 2014, 13 pages.
PCT International Search Report and Written Opinion, PCT/US2014/055509, dated Dec. 2, 2014, 15 pages.
PCT International Search Report and Written Opinion, PCT/US2014/064144, dated Jan. 27, 2015, 7 pages.
Florian, et al., Dynamic Spectral Analysis of Event-Related EEG Data, Electroencephalography and Clinical Neurophysiology, 1995, 95:393-396.
Prerau, et al., Tracking Non-Stationary Spectral Peak Structure in EEG Data, In Engineering in Medicine and Biology Society (EMBC), 2013 35th Annual International Conference of the IEEE, pp. 417-420.
Sleigh, et al., Cortical Entropy Changes with General Anaesthesia: Theory and Experiment, Physiological Measurement, 2004, 25:921-934.
Ting, et al., Spectral Estimation of Nonstationary EEG Using Particle Filtering with Application to Event-Related Desynchronization (ERD), IEEE Transactions on Biomedical Engineering, 2011, 58(2):321-331.
European Patent Office, Extended European Search Report, Application No. 14818074.8, dated Feb. 8, 2017.
International Search Report and Written Opinion dated Nov. 28, 2014 for International Application No. PCT/US2014/044720.
Absalom, et al., Closed-Loop Control of Anesthesia Using Bispectral Index, Anesthesiology, 2002, 96(1):67-73.
Absalom, et al., Closed Loop Anesthesia: Are We Getting Close to Finding the Holy Grail?, Anesthesia & Analgesia, 2011, 112(3):516-518.
Andrews, et al., The Chronux Manual, Aug. 16, 2008, 178 pages.
Araki, et al., Computer Control of Physiological States of Patients Under and After Surgical Operation, Annual Reviews in Control, 2005, 29:229-236.
Barras, et al., Total Intravenous Anesthesia on the Battlefield, The Army Medical Department Journal, 2009, pp. 68-72.
Bellville, et al., Servo Control of General Anesthesia, Science, 1957, 126:827-830.
Besch, et al., Occurrence of and Risk Factors for Electroencephalogram Burst Suppression During Propofol-Remifentanil Anaesthesia, British Journal of Anaesthesia, Advance Access Published Aug. 8, 2011, 8 pages.
Besthorn, et al., EEG Coherence in Alzheimer Disease, Electroencephalography and Clinical Neurophysiology, 1994, 90:242-245.
Bickford, Automatic Electroencephalographic Control of General Anesthesia, EEG Clin. Neurophysiol., 1950, 2:93-96.
Bickford, Use of Frequency Discrimination in the Automatic Electroencephalographic Control of Anesthesia (Servo-Anesthesia), EEG Clin. Neurophysiol., 1951, 3:83-86.
Blanco, et al., Time-Frequency Analysis of Electroencephalogram Series. III. Wavelet Packets and Information Cost Function, Physical Review E, 1998, 57(1):932-940.
Bonmassar, Resistive Tapered Stripline (RTS) in Electroencephalogram Recordings During MRI, IEEE Transactions on Microwave Theory and Techniques, 2004, 52(8):1992-1998.
Bourguignon, et al., A Sparsity-Based Method for the Estimation of Spectral Lines From Irregularly Sampled Data, IEEE Journal of Selected Topics in Signal Processing, 2007, 1(4):575-585.
Breshears, et al., Stable and Dynamic Cortical Electrophysiology of Induction and Emergence with Propofol Anesthesia, PNAS, 2010, 107(49):21170-21175.
Candes, et al., Enhancing Sparsity by Reweighted l1 Minimization, J. Fourier Anal. Appl., 2008, 14:877-905.
Chemali, et al., Burst Suppression Probability Algorithms: State-Space Methods for Tracking EEG Burst Suppression, J. Neural. Eng., 2013, 10(5):056017.
Ching, et al., A Neurophysiological-Metabolic Model for Burst Suppression, PNAS, 2012, 109(8)3095-3100.
Cimenser, et al., Tracking Brain States Under General Anesthesia by Using Global Coherence Analysis, PNAS, 2011, 108(21):8832-8837.
Ciuciu, et al., A Half-Quadratic Block-Coordinate Descent Method for Spectral Estimation, Signal Processing, 2002, 82:941-959.
Cotten, et al., Closed-Loop Continuous Infusions of Etomidate and Etomidate Analogs in Rats, Anesthesiology, 2011, 115(4):764-773.
Dodson, et al., Postoperative Effects of Methylphenidate, British Journal of Anaesthesia, 1980, 52:1265-1270.
Gentilini, et al., Modeling and Closed-Loop Control of Hypnosis by Means of Bispectral Index (BIS) with Isoflurane, IEEE Transactions on Biomedical Engineering, 2001, 48(4874-889.
Glass, Automated Control of Anesthesia Ten Years Later: Futuristic Novelty or Present Day Reality, Can. J. Anesth./J. Can. Anesth., 2010, 57:715-719.
Goldman, et al., Acquiring Simultaneous EEG and Functional MRI, Clinical Neurophysiology, 2000, 111:1974-1980.
Hahn, et al., Closed-Loop Anesthetic Drug Concentration Estimation Using Clinical-Effect Feedback, IEEE Transactions on Biomedical Engineering, 2011, 58(1):3-6.

(56) References Cited

OTHER PUBLICATIONS

Hahn, et al., A Direct Dynamic Dose-Response Model of Propofol for Individualized Anesthesia Care, Journal of Latex Class Files, 2007, 6(1):1-8.

Hemmerling, et al., A Randomized Controlled Trial Demonstrates that a Novel Closed-Loop Propofol System Performs Better Hypnosis Control than Manual Administration, Can. J. Anesth/J. Can. Anesth., 2010, 57:725-735.

John, et al., Invariant Reversible QEEG Effects of Anesthetics, Consciousness and Cognition, 2001, 10:165-183.

Lemieux, et al., Recording of EEG During fMRI Experiments: Patient Safety, MRM, 1997, 38:943-952.

Leslie, et al., Closed Loop Control of Sedation for Colonoscopy Using the Bispectral Index, Anaesthesia, 2002, 57:690-709.

Liley, et al., Propofol and Remifentanil Differentially Modulate Frontal Electroencephalographic Activity, Anesthesiology, 2010, 113:292-304.

Lin, et al., EEG-Based Drowsiness Estimation for Safety Driving Using Independent Component Analysis, IEEE Transactions on Circuits and Systems-I: Regular Papers, 2005, 52(12):2726-2738.

Liu, et al., Titration of Propofol for Anesthetic Induction and Maintenance Guided by the Bispectral Index: Closed-Loop Versus Manual Control, Anesthesiology, 2006, 104:686-695.

Liu, et al., Feasibility of Closed-Loop Titration of Propofol Guided by the Bispectral Index for General Anaesthesia Induction: A Prospective Randomized Study, European Journal of Anaesthesiology, 2006, 23:465-469.

Liu, et al., Neural Origin of Spontaneous Hemodynamic Fluctuations in Rats Under Burst-Suppression Anesthesia Condition, Cerebral Cortex, 2011, 21:374-384.

Locher, et al., A New Closed-Loop Control System for Isoflurane Using Bispectral Index Outperforms Manual control, Anesthesiology, 2004, 101:591-602.

Lotte, et al., A Review of Classification Algorithms for EEG-Based Brain-Computer Interfaces, Journal of Neural Engineering, 2007, 4:R1-R13.

Martin, et al., Investigating Neural-Hemodynamic Coupling and the Hemodynamic Response Function in the Awake Rat, NeuroImage, 2006, 32:33-48.

Mirsattari, et al., Treatment of Refractory Status Epilepticus With Inhalational Anesthetic Agents Isoflurane and Desflurane, Arch. Neurol, 2004, 61:1254-1259.

Molaee-Ardekani, et al., Delta Waves Differently Modulate High Frequency Components of EEG Oscillations in Various Unconsciousness Levels, Proceedings of the 29th Annual International Conference of the IEEE EMBS, 2007, pp. 1294-1297.

Morley, et al., Closed Loop Control of Anaesthesia: An Assessment of the Bispectral Index as the Target of Control, Anaesthesia, 2000, 55:953-959.

Mortier, et al., Closed-Loop Controlled Administration of Propofol Using Bispectral Analysis, Anesthesia, 1998, 53:749-754.

Orsini, et al., Propofol Infusion Syndrome: Case Report and Literature Review, Am. J. Health-Syst. Pharm., 2009, 66:908-915.

Pritchett, et al., Power Analysis of Gamma Frequencies (30-47Hz), Adjusting for Muscle Activity (80-97Hz), in Anesthesia: A Comparison Between Young Adults, Middle-Aged and the Elderly, 30th Annual International IEEE EMBS Conference, 2008, pp. 825-830.

Purdon, Multimodal Neuroimaging with Simultaneous Electroencephalogram and High-Field Functional Magnetic Resonance Imaging, Master Thesis Submitted to the Harvard-MIT Division of Health Sciences and Technology, Jun. 2005.

Purdon, et al., Electroencephalogram Signatures of Loss and Recovery of Consciousness from Propofol, PNAS, Published Online Mar. 4, 2013, pp. E1142-E1151.

Puri, et al., Closed-Loop Anaesthesia Delivery System (CLADS(TM)) Using Bispectral Index: A Performance Assessment Study, Anaesthesia and Intensive Care, 2007, 35(3):357-362.

Roche-Labarbe, et al., Coupled Oxygenation Oscillation Measured by NIRS and Intermittent Cerebral Activation on EEG in Premature Infants, NeuroImage, 2007, 36:718-727.

Rossetti, et al., Refractory Status Epilepticus, Effect of Treatment Aggressiveness on Prognosis, Arch. Neurol., 2005, 62:1698-1702.

Sacchi, et al., Interpolation and Extrapolation Using a High-Resolution Discrete Fourier Transform, IEEE Transactions on Signal Processing, 1998, 46(1)31-38.

\* cited by examiner

SYSTEMS AND METHODS FOR TRACKING NON-STATIONARY SPECTRAL STRUCTURE AND DYNAMICS IN PHYSIOLOGICAL DATA

CROSS-REFERENCE TO RELATED APPLICATIONS

The present application represents the U.S. National Stage of International Application No. PCT/US2014/044720, filed Jun. 27, 2014 which is based on, claims priority to, and incorporates herein by reference in its entirety U.S. Provisional Application Ser. No. 61/840,093 filed Jun. 27, 2013, and entitled "METHODS AND SYSTEMS FOR TRACKING NON-STATIONARY SPECTRAL PEAK STRUCTURE IN EEG DATA."

STATEMENT REGARDING FEDERALLY SPONSORED RESEARCH

This invention was made with government support under DP2 OD006454 awarded by the National Institutes of Health, and under IIS-0643995 awarded by the National Science Foundation. The government has certain rights in the invention.

BACKGROUND

The present disclosure generally relates to systems and methods for monitoring and/or controlling states of a subject, and more specifically to systems and methods for monitoring and/or controlling states of a subject using a model-based characterization of the dynamic time-frequency structure associated with physiological data.

In the case of surface recordings of brain activity, it was demonstrated over 75 years ago that central nervous system changes, such as those occurring during sleep or as a result of administration of an anesthetic, are observable via neural EEG recordings, which measure electrical impulses in the brain through electrodes placed on the scalp. As a consequence, it was postulated that EEG information could be used to track in real time the brain states of patients, for instance during sleep, or under sedation and general anesthesia, the same way that an electrocardiogram could be used to track the state of the heart and the cardiovascular system.

Tools used by clinicians for monitoring brain states of patients include physiologically and EEG-based systems developed to help measure neural network activity resulting from certain biological processes, task activity, sleep, anesthetic administration, and other clinical procedures. For example, such monitoring systems are used to track the level of consciousness of a patient undergoing general anesthesia or sedation in the operating room and intensive care unit. Using proprietary algorithms that combine spectral and entropy information derived from EEG data, such systems provide feedback through partial or amalgamized representations of the acquired signals for use in identifying the brain state of a patient. In some scenarios, direct manipulation of the central nervous system, often performed using pharmacological approaches, is facilitated using such systems by way of controlling the level unconsciousness, amnesia, analgesia, and immobility of a patient. For example, during sleep, EEG, EOG, EMG, and respiration data is monitored in clinical or home settings, and then evaluated through visual analysis to diagnose sleep and respiratory disorders.

In order to examine specific spectral signatures of underlying neural activity, it has been an emerging practice to compute time-frequency representations of the acquired EEG data, using techniques including but not limited to spectrograms (FFT, Hanning window), multitaper spectrograms, wavelet transforms, Gabor transforms, and chirplet transforms. Different approaches previously proposed characterized measured neural rhythms at several discrete time periods, using methods that describe time-varying spectral signatures qualitatively. For instance, one attempt for tracking time-frequency features included modeling spectral content using pure sinusoids that have non-stationary peaks and amplitudes. Specifically, the sum of more than one sinusoid model was used to track multiple simultaneously-evolving oscillations. While this previous approach may be adequate for tracking pure sinusoids produced by artificial or mechanical systems, such pure sinusoids are almost never present in physiological systems.

For example, measured EEG signals often exhibit broadband peaks in the time-frequency domain, the full structure of which can provide important information about the underlying neural activity. In particular, the specific form of a spectral peak, describing EEG data acquired during, say, administration of propofol during general anesthesia, can provide information about a patient's depth-of-consciousness. Hence, current methods that employ sinusoidal models of time-frequency structure are lacking since such methods collapse broadband physiological oscillations to a single frequency, thereby ignoring information content present in the peak bandwidth and structure. It is therefore necessary to devise a system in which the full spectral structure and the information contained there in are retained.

Considering the above, there continues to be a need for systems and methods to quantitatively and accurately analyze physiological data dynamics for monitoring patients and based thereon, provide systems and methods for controlling patient states, such as during sedation, general anesthesia, sleep, medically induced coma, hypothermia, drug delivery, or other natural or pharmacologically-mediated dynamic neural scenarios.

SUMMARY

The present disclosure overcomes drawbacks of previous technologies by providing systems and methods for tracking the dynamic time-frequency structure present in physiological data acquired from a subject, such as spectral peaks, for purposes including, data analysis, and monitoring and/or controlling physiological states of the subject. Specifically, the present disclosure provides systems and methods that utilize a statistical sampling approach to estimate, either concurrently or simultaneously, parameters included in models describing dynamic components of physiological signals in the time-frequency domain.

In particular, an approach is described that includes decomposing time-varying spectra into multiple concurrent spectral peaks using parametric or semi-parametric models of the peak structure, and contemporaneously or simultaneously tracking their time-varying properties. Time-varying parameters of these spectral decomposition functions include spectral features such as instantaneous peak frequency, amplitude, and bandwidth. In addition to the form of this specific model, a framework is provided by which such methodology can be broadly applied to any physiological system using a wide array of parametric or semi-parametric models of time-frequency structure and temporal dynamics.

In this manner, the present disclosure provides an approach whereby it is possible retain important information contained in the full spectral structure, by decomposing the power spectrum into specific components of the overall spectra, such as individual spectral peaks, each with a specific shape as function of frequency, which could be broad-band. Such "spectral decomposition functions" are functional representations of the spectral components, defined using structurally-interpretable parameters such as the peak frequency, amplitude, bandwidth, as well as overall spectral shape of the oscillations. In doing so, a more complete representation of the power spectrum could be achieved. Moreover, since the frequency content of physiological systems may change over time, such spectral decomposition functions are allowed to vary in time as well. This is achieved using a dynamic framework that allows the spectral decomposition function parameters to vary over time, perhaps as a function of intrinsic or extrinsic covariates.

In accordance with one aspect of the present disclosure, a system for tracking dynamic structure in physiological data is provided. The system includes at least one input configured to receive electroencephalography ("EEG") data acquired from a subject, and a processor configured to receive the EEG data from the at least one input and assemble a time-frequency representation of signals from the EEG data. The processor is also configured to generate a dynamic model of at least one non-stationary spectral peak using the time-frequency representation and a user indication, and apply the dynamic model in a parameter estimation algorithm to compute concurrent estimates of peak parameters describing the at least one non-stationary spectral peak, the peak parameters including a peak frequency, a peak bandwidth and a peak amplitude. The processor is further configured to track the peak parameters of the at least one non-stationary spectral peak over time.

In accordance with another aspect of the present disclosure, a method for tracking dynamic structure in physiological data is provided. The method includes providing electroencephalogram ("EEG") data acquired from a subject, and assembling a time-frequency representation of signals from the EEG data. The method also includes generating a dynamic model of at least one non-stationary spectral peak using the time-frequency representation and a user indication, and applying a dynamic model of at least one non-stationary spectral peak in a parameter estimation algorithm to compute concurrent estimates of peak parameters describing the at least one non-stationary spectral peak, the peak parameters including a peak frequency, a peak bandwidth and a peak amplitude. The method further includes tracking the peak parameters of the at least one spectral peak over time.

In accordance with another aspect of the present disclosure, a system for tracking dynamic structure in physiological data is provided. The system includes at least one input configured to receive physiological data acquired from a subject and a processor configured to receive the physiological data from the at least one input, and assemble a time-frequency representation of signals from the physiological data. The processor is also configured to generate a dynamic model of at least one non-stationary spectral feature using the time-frequency representation and a user indication, and apply the dynamic model in a parameter estimation algorithm to compute concurrent estimates of spectral parameters describing the at least one non-stationary spectral feature. The processor is further configured to track the spectral parameters of the at least one non-stationary spectral feature over time.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

DETAILED DESCRIPTION

Figure 1A:
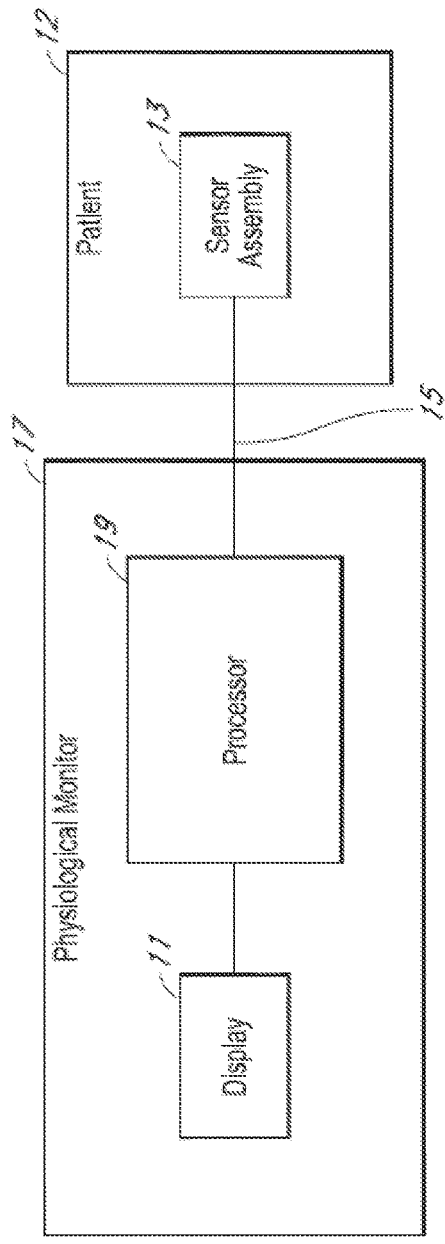
FIGS. 1A-B are schematic block diagrams of a physiological monitoring system.

Spectral analysis is an important tool for analyzing the time-frequency structure of physiological data. The traditional approach to clinical interpretation of electrophysiological recordings is to visually examine time domain waveforms, associating different waveform morphologies with physiology, pathophysiology, or clinical outcomes. Visual time-series analysis, however, is a highly subjective and time-consuming process, and spectral analysis can provide valuable information difficult to observe in the time-domain. For example, in sleep medicine, sleep studies record patient EEG, EMG, EOG, and respiratory data. These data records, lasting up to 10 hours in duration, are broken into 30-second segments, each of which must be visually interpreted in the time-domain. This scenario makes it extremely difficult to effectively track non-stationary properties of the sleep signal over time, which may provide important information for characterizing clinically-relevant features of a patient's sleep. In another example, general anesthetic and sedative drugs induce stereotyped non-stationary oscillations in the EEG that are much easier to interpret when analyzed in the time-frequency domain using spectral analysis. The ability to track the time-varying properties of these oscillations could be used to track, for example, changes in drug dosage or administration, or changes in patient's level of arousal due to external stimuli.

Systems and methods, as provided herein, may be applied to physiological data acquired from a subject under a number of clinical or experimental scenarios, including but not restricted to sleep, drug delivery, general or local anesthesia, sedation, coma, hyperthermia, and so on, for purposes of monitoring and/or controlling the physiological state of the subject. As will be described, the present disclosure details an approach that quantitatively describes the dynamic time-frequency structure of physiological signals, providing models that capture non-stationary signal properties present therein, as well as respective temporal variation of such properties. Specifically, the time-frequency representation of acquired physiological data may be decomposed into parametric, or semi-parametric functions specific to the forms of the spectral peak structures, the functions including parameters such as, instantaneous peak frequency, amplitude, and bandwidth. A time-varying model may then be defined to describe the time variation of the parameters. As such, using an estimation procedure in conjunction with time-frequency physiological data and models, the parameters may be fit at each point in time. In this manner, multiple concurrent non-stationary components of a physiological signal can be tracked in the time-frequency domain.

The following describes a specific implementation for analyzing EEG data under various scenarios, such as general anesthesia, sedation, or sleep, using a statistical sampling parameter estimation algorithm, Gaussian and Gamma shaped models of spectral peak structure, and a linear Gaussian model of peak temporal dynamics. However, it may be appreciated by one skilled in the art that various types physiological data acquired under multiple scenarios may be utilized, and be considered to be within the scope of the present invention. For instance, non-limiting examples of physiological data may include data obtained from electroencephalography ("EEG"), electromyography ("EMG"), electrocorticography ("ECoG"), local field potentials ("LFP"), electrocardiography ("ECG"), electrooculography ("EOG"), galvanic skin response ("GSR"), oxygen saturation ($SAO_2$), ocular microtremor ("OMT"), and so forth. In addition, as will be described, the specific model presented relates to a more general statistical framework, which may be applied in describing time-frequency dynamics of various physiological monitoring conditions or scenarios.

Spectral Peak Parameter State Models

The following describes a specific implementation of an approach for dynamic time-frequency peak tracking, which is applied to simulated EEG data, as well as EEG data acquired from a subject during the administration of propofol anesthesia. This serves as a concrete example in a general dynamic time-frequency tracking approach.

Given time-frequency observations, such as those generated from EEG signal data, over discrete times $t \in \{1, \ldots, T\}$, and fixed-width frequency bins centered at frequencies $f \in \{1, \ldots, F\}$, a matrix can be constructed of the spectral domain observations, namely $$Y = \begin{pmatrix} y_{1,i} & \cdots & y_{1,T} \\ \vdots & \ddots & \vdots \\ y_{F,i} & \cdots & y_{F,T} \end{pmatrix} \quad (1)$$

such that $y_{t,f}$ is the magnitude of the power spectrum at time t within the frequency bin f.

In general, Y may be any time-frequency representation, such as a spectrogram (FFT, Hanning window), multitaper spectrogram, wavelet transform, Gabor transform, or chirplet transform of any physiological data, including EEG, EMG, ECoG, LFP, ECG, EOG, GSR, $SAO_2$, and OMT. In a general formulation, the $y_{t,f}$ elements may include complex values representing the magnitude and phase of the spectral domain observations, as well as transformations such as a logarithmic or decibel transformation, for instance. The data could also be transformed prior to computing the time-frequency representation, for instance, by combining information across a plurality of electrodes across space, as in an EEG montage. Y may also include time-frequency data from combinations of various physiological data sources. $y_{t,f}$ In accordance with methods described in the present disclosure, an estimate of Y, namely $\hat{Y}$, is constructed from a function or a set of functions with time-varying parameters, which may represent multiple concurrent non-stationary spectral peaks. To compute $\hat{y}_{t,f}$, which are estimates of $y_{t,f}$, the spectral observations may be modeled as a linear combination of N discrete non-stationary peaks in spectral power, such that $$\hat{y}_{t,f} = \sum_{n=1}^{N} \Omega_n(t, f, \theta_t^n) + \varepsilon_{y_{t,f}}, \quad (2)$$

where $\Omega_n(t,f,\theta_t^n)$ is the magnitude of the $n^{th}$ spectral peak, and $\varepsilon_{y_{t,f}}$ is the observation noise at time t within frequency bin f. Each spectral peak is characterized at time t by its own set of parameters $\theta_t^n$, which describes its time-varying amplitude $A_t$, peak frequency $F_t$, and bandwidth $B_t$. Of note is that this particular model defines the estimate of the time-frequency representation of the data as a linear mixture model. In general, $\hat{Y}$ can be formulated as any linear or non-linear combination of spectral decomposition functions.

The temporal evolutions of the parameters may be defined as random walks, such that for a given parameter x $$x_t = x_{t-1} + \varepsilon_{x_t}, \quad (3)$$

where $\varepsilon_{x_t} \sim N(0, \sigma_{x_t}^2)$.

The state variance parameters may also be defined as random walks, $$\sigma_{x_t}^2 = \sigma_{x_{t-1}}^2 + \varepsilon_v, \quad (4)$$

where $\varepsilon_v \sim N(0, \sigma_v^2)$ and v is a constant.

In addition, the observation noise may be modeled as a function of frequency f $$\varepsilon_{y_{t,f}} = N(0, \sigma_{y_t}^2 f^{-p}) \quad (5)$$

which reflects the $1/f^p$ noise phenomenon, of power factor p, widely observed in physiological EEG data. The observation noise variance also evolves as a random walk with constant variance $$\sigma_{y_t}^2 = \sigma_{y_{t-1}}^2 + \varepsilon_v, \quad (6)$$

where $\varepsilon_v \sim N(0, \sigma_v^2)$ as in Eqn. 4. Thus, the parameter vector for each spectral peak is $\theta_t^n = \{A_t, F_t, B_t, \sigma_{A_t}^2, \sigma_{F_t}^2, \sigma_{B_t}^2\}$.

While the above-described model represents parameter temporal dynamics as linear and having Gaussian noise, and observations as having a $1/f^p$ noise, other linear or non-linear models with Gaussian or non-Gaussian state and observation noise may be used as well. Moreover, interactions between specific parameters, as well as relationships between parameters and other data sources or external correlates, such as drug concentration, may also be modeled. Additionally, spectral phase structure may be modeled, in cases where $y_{t,f}$ elements are complex.

Observation Model Components

Given a framework for characterizing the time-frequency representation of physiological data as the combination of spectral features, the functional forms of these features may then be defined. In particular, with respect to spectral features commonly observed in EEG data, given $\theta_t^n$, the observation model $$\Omega_n(t, f, \theta_t^n) = \exp\left(A_t - \frac{(f - F_t)^2}{2B_t}\right) \quad (7)$$

can be used to characterized the spectral peak as a Gaussian shaped function with amplitude $\exp(A_t)$, peak frequency $F_t$ and bandwidth $B_t$.

The Gaussian shaped function, however, may not always be appropriate model of peak structure. Since frequency, by definition, is bounded at zero, the structure of the spectral peaks with low peak frequencies may be highly asymmetrical. Specifically, this is evident in the EEG slow/delta wave rhythms observed in sleep and general anesthesia. Therefore, an alternative example of a model for the peak structure may be defined as:

$$\Omega_n(t, f, \theta_t^n) = \frac{\exp(A_t)}{v}\left[f^{(k-1)}\exp\left(-\frac{f}{\varphi}\right)\right], \quad (8)$$

where $v = \exp(1-k)[(k-1)\varphi]^{(k-1)}$, $k = 1/2B_t(\sqrt{F_t^2(4B_t+F_t^2)} + 2B_t + F_t^2)$ and $\varphi = 1/2F_t(\sqrt{F_t^2(4B_t+F_t^2)} - F_t^2)$. In this manner, spectral features based on the shape of a Gamma distribution with amplitude $\exp(A_t)$, peak frequency $F_t$, bandwidth $B_t$, and shape and scale parameters, k, and $\varphi$, respectively, may be characterized.

In general, various parametric models of spectral structures can be used, including those based on other continuous distributions such as lognormal, Gompertz, Chi-squared, inverse-Chi-squared, exponential, inverse Gamma, inverse Gaussian, Beta, and so on. Additionally, semi-parametric functions may also be used, to include splines and Bezier curves, for example.

Likelihood and Goodness-of-Fit

Given N simultaneous, or concurrent, spectral features defined by a function or set of functions, a parameter vector and observation noise vector can be constructed for each time t as follows:

$$\Theta_t = \left\{\theta_t^1, \ldots, \theta_t^N, \{\sigma_{y_{t,f}}^2\}^{f=1,\ldots,F}\right\}^{t=1,\ldots,T} \quad (9)$$

For a given $\Theta_t$, the probability at time t of the observed data given the model, $Pr(Y_t|\Theta_t)$, which is proportion to the instantaneous likelihood, can be computed as follows:

$$Pr(Y_t | \Theta_t) \propto L(\Theta_t) = \quad (10)$$

$$\exp\left(-\sum_{f=1}^{F}\frac{(\mathrm{re}\{y_{t,f}\} - \mathrm{re}\{\hat{y}_{t,f}\})^2}{2(\sigma_{y_{t,f}}^2)} - \sum_{f=1}^{F}\frac{(\mathrm{im}\{y_{t,f}\} - \mathrm{im}\{\hat{y}_{t,f}\})^2}{2(\sigma_{y_{t,f}}^2)}\right).$$

In the spectral peak example described, the parameter vector may be $$\Theta_t = \{\theta_t^N, \sigma_{y_t}^2, p\} \quad (11)$$

Since the $y_{t,f}$ elements represent only the magnitude of the time-frequency representation of the data, the imaginary component of the likelihood disappears, and $\sigma_{y_{t,f}}^2 = \sigma_{y_t}^2 f^{-p}$, so that the likelihood becomes:

$$Pr(Y_t | \Theta_t) \propto L(\Theta_t) = \exp\left(-\sum_{f=1}^{F}\frac{(y_{t,f} - \hat{y}_{t,f})^2}{2(\sigma_{y_t}^2 f^{-p})}\right). \quad (12)$$

Given any dynamic model of time-frequency decomposition functions, the general likelihood expression of Eqn. 10 and the data, a total likelihood of the model $L_{total}(\Theta)$ given the data can be computed by taking the product of the likelihood over time, or the sum of the log-likelihood over time:

$$L_{total}(\Theta) = \prod_{t=1}^{T}L(\Theta_t) = \sum_{t=1}^{T}\log(L(\Theta_t)). \quad (13)$$

The total likelihood may then be used to assess a goodness-of-fit, and to perform a model comparison. Specifically, it is possible in this approach to use a relative goodness-of-fit indicator for the different selected, or generated, models to compare hypotheses related to dynamic features of the underling physiological time-frequency structure, such as a number of peaks, peak temporal dynamics, relationships between the structure of different peaks, relationships between peak structure and external correlates, differences in peak structure across time/space, differences in peak structures across groups/pathologies/experimental conditions, and so forth.

Therefore, in some aspects, the modeling framework presented herein may be further implemented as a powerful tool for data analysis, as it may be utilized for quantitative assessment for different theories related to the dynamical properties of a physiological system.

Parameter Estimation

Given physiological data, the model framework, and a metric for assessing goodness-of-fit, it is possible to provide estimates for the model parameters. In one particular embodiment, as will be described, a statistical sampling method called a bootstrap particle filter may be applied for estimating parameters. However, alternative estimation procedures could also be employed, such as other sequential importance sampling ("SIS") methods, Kalman filters, variational Bayes estimators, and the Expectation-Maximization ("EM") algorithm. Additionally, explicit model-specific estimates can also be computed. Specifically, the purpose of such estimation procedures is to produce an estimate of the distribution of each of the model parameters during each time period of a time-frequency representation. Given such distribution, statistics related to individual or multiple spectral peaks present in the data can be computed, changes in spectral structure can be tracked, compute functions of this distribution that are related to clinical or disease states, and compute the statistical uncertainty of all of these quantities.

Referring to the example spectral peak model presented herein, as mentioned, the parameter vector of Eqn. 11 and likelihood of Eqn. 12 may be used to construct a bootstrap particle filter, which is a Bayesian sequential importance sampling method that generates a set of P parameter vectors, or particles, whose distributions approximates the posterior distribution, $Pr(Y_t|\Theta_t)$. In some aspects, the initial particle values may be drawn from a pre-defined proposal density, for example, using information provided by a user. Particularly, in dealing with physiological data under experimental conditions, information relating to understood characteristics of spectral peaks may be used to inform the choice of proposal densities, since the time-frequency structure of the data may be well-known. This allows judicious selection of priors for each of the parameters in questions, given specific knowledge of the underlying physiology such as number of peaks, peak frequency, amplitude, and bandwidth. For example, in the case of EEG during propofol anesthesia, generally two peaks arise in the time-frequency domain during loss of consciousness, and hence, N=2. Since the peak frequency, amplitude and bandwidth parameters of each of these oscillations have been previously described, proposal densities reflecting this knowledge may be used for each of the peaks.

Therefore, for each spectral peak parameter x at time 0, a proposal density may be drawn in accordance with $$Pr(x_0) \sim U(x_{min}, x_{max}), \quad (14)$$

where each parameter may be distributed uniformly between experimentally known bounds. For example, when human subjects close their eyes, an EEG oscillation is generally observed in the occipital portion of the brain, and exhibits a peak frequency that falls between 8-12 Hz. Therefore, a prior for peak frequency of this particular "alpha" oscillation could be uniform between 8 and 12 Hz.

In some aspects, it is also possible to use non-uniform distributions of physiologically-known parameter values, such as a Gaussian centered distributions, or specialized distributions such as the beta distribution for binomial data or inverse-chi-squared for priors on variance. By contrast, in case that no physiological precedent is available, a broad uniform density may be utilized. The multidimensional proposal density for the entire parameter vector is called $\pi(\Theta_0)$.

In accordance with the present invention, an iterative bootstrap particle filter procedure may be performed as follows, given a set of particles P, where $\rho_t^i$ is the $i^{th}$ particle at time t, and contains values for $\Theta_t$, the vector of all model parameters at time t Specifically, a bootstrap particle filter procedure for the example EEG model described may include steps as follows:

1) Initialize the particles using the proposal densities, such that at t=0, $\rho_0^i \sim (\Theta_0)$.
2) For each time $t \in \{2, \ldots, T\}$, for all particles $\{\rho_t^1, \ldots, \rho_t^P\}$:
   a) Sample a new value for each particle based on the one-step prediction density, $\rho_{t|t-1}^i \sim Pr(\Theta_t|\rho_{t-1}^i)$, by applying Eqn. 3 and 4. The absolute value may be taken to ensure that each parameter is positive definite.
   b) Compute a weight $w^i$ such that $w^i = L(\rho_{t|t-1}^i)$, and normalized so that $$\sum_{i=1}^{P} w^j = 1.$$

c) Resample the collection of particles according to the set of weights $Pr(\rho_t^i = \rho_{t|t-1}^j) = w^j$.
   d) The parameter estimate $\hat{\Theta}_t$ may be defined as the component-wise median of $\{\rho_t^1, \ldots, \rho_t^P\}$. Confidence bounds with a significance $\alpha$ can be computed using the component-wise $\alpha/2$ and $1-\alpha/2$ percentiles of $\{\rho_t^1, \ldots, \rho_t^P\}$.

An estimated filtered time-frequency representation may then be reconstructed using the parameter estimate $\hat{\Theta}$ and Eqns. 2, 7, and 8, which describe the spectral decomposition functions and the way in which they are combined to estimate the time-frequency representation of the data.

Figure 1B:
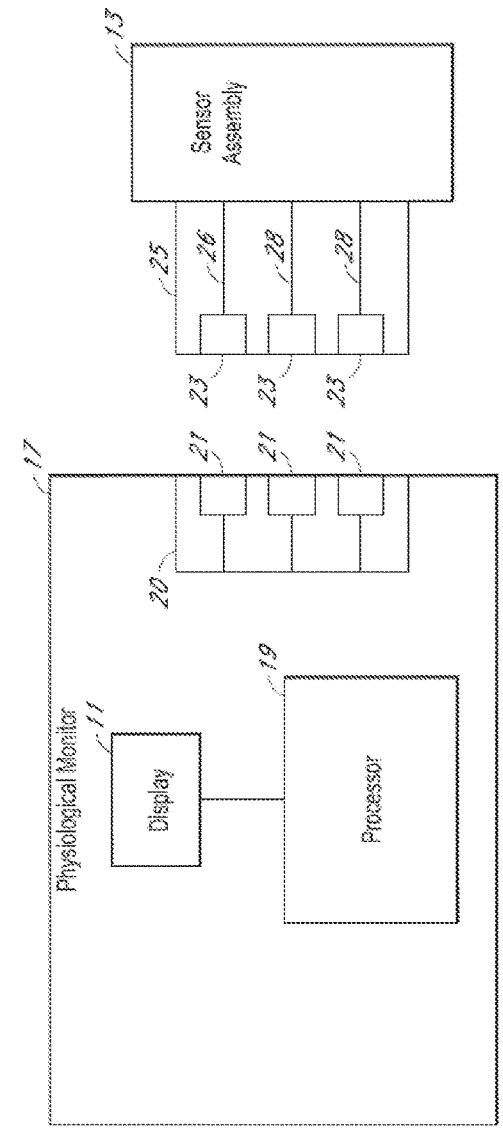

Referring now specifically to the drawings, FIGS. 1A and 1B illustrate example monitoring systems and sensors that can be used to provide physiological monitoring of a subject during physiological processes such as sleep, and under pharmacological-induced states such as general anesthesia or sedation.

For example, FIG. 1A shows an embodiment of a physiological monitoring system 10. In the physiological monitoring system 10, a medical patient 12 is monitored using one or more inputs, such as a sensor assembly 13, each of which transmits a signal over a cable 15 or other communication link or medium to a physiological monitor 17. In some aspects, an input (not shown) may be configured to receive an indication from a user. The physiological monitor 17 includes a processor 19 and, optionally, a display 11. The sensor assembly 13 includes physiological sensing elements such as, for example, electrical EEG sensors, EMG sensors, GSR sensors, depth electrodes, or the like. The sensor assembly 13 can generate respective signals by measuring physiological parameters of the patient 12. The signals are then processed by one or more processors 19. The one or more processors 19 then communicate the processed signal to the display 11 if a display 11 is provided. In an embodiment, the display 11 is incorporated in the physiological monitor 17. In another embodiment, the display 11 is separate from the physiological monitor 17. The monitoring system 10 is a portable monitoring system in one configuration. In another instance, the monitoring system 10 is a pod, without a display, and is adapted to provide physiological parameter data to a display.

For clarity, a single block is used to illustrate the sensor assembly 13 shown in FIG. 1A. It should be understood that the sensor assembly 13 shown is intended to represent one or more sensors and adapted to receive signals from the patient 12. For example, the sensor assembly 13 can include EEG, EMG, ECoG, LFP, ECG, EOG, GSR, and $SAO_2$ sensors, as well as respiration sensors and other sensors used for other physiological recordings. Various combinations of numbers and types of sensors, as mentioned, are suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensor assembly 13.

As shown in FIG. 1B, each sensor 13 in a sensor assembly can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors, one or more additional cables 25 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

Figure 2:
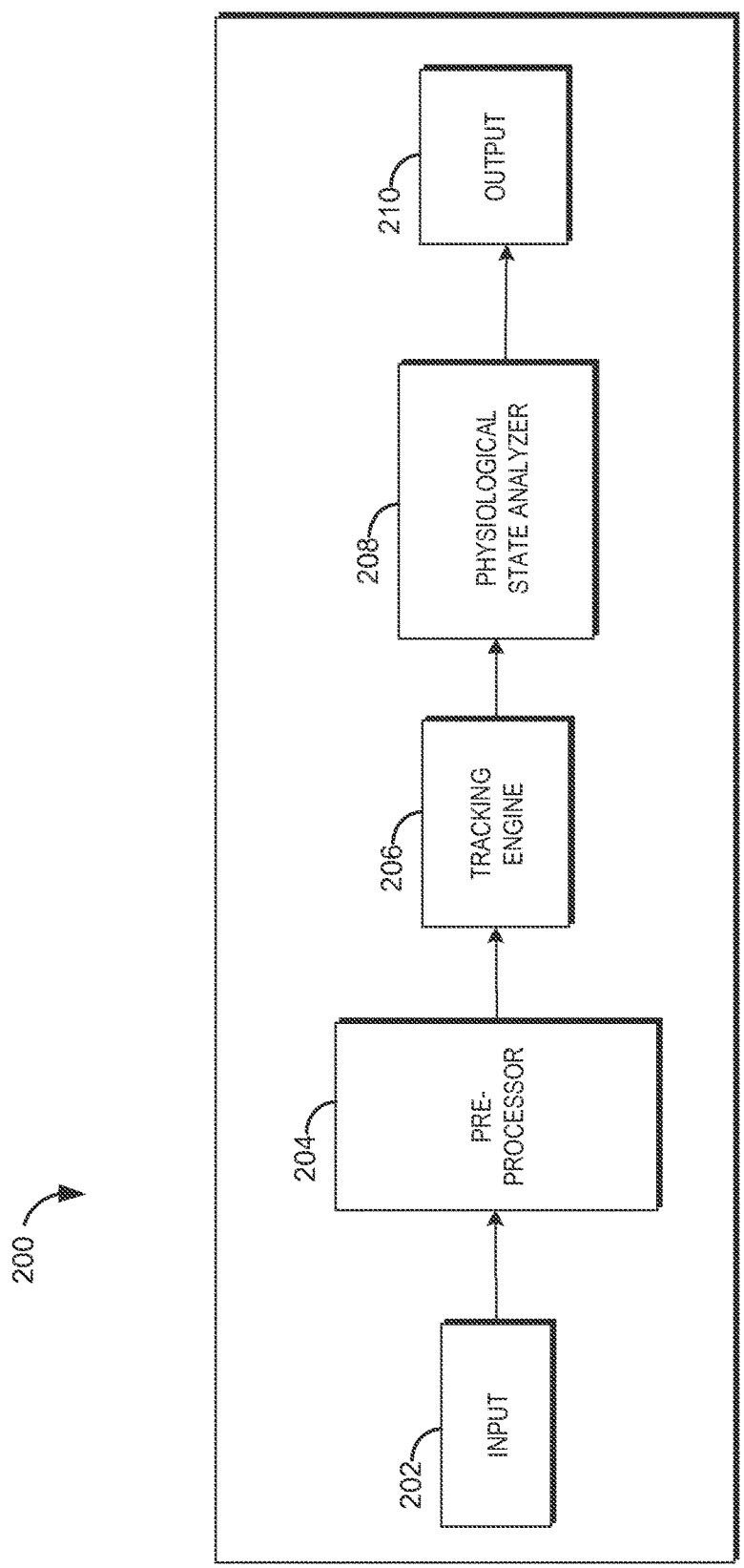
FIG. 2 is a schematic block diagram of an example system for improved spectral analysis, in accordance with the present disclosure.

Referring to FIG. 2, an example system 200 for use in carrying out steps in accordance with the present disclosure, is illustrated. The system 200 may include an input 202, a pre-processor 204, a spectral peak tracking engine 206, a physiological state analyzer 208, and an output 210. Some or all of the modules of the system 200 can be implemented by a physiological patient monitor as described above with respect to FIG. 1.

The input 202 may be configured to accept an indication from a user related to a particular subject profile such as a patient's age, height, weight, gender, or the like, as well as a drug administration information, such as timing, dose, rate, and the like. In some aspects, the indication may also include information related to the physiological conditions or scenarios of a subject being monitored by system 200. For example, such physiological conditions may include the subject being under pharmacological-induced states, such as general anesthesia or sedation, or while asleep, or while undergoing a medical procedure. Additionally, the indication may include information directed to selection of particular spectral decomposition functions and temporal models that could describe physiological data acquired from the subject, including initial priors for model parameters chosen based on specified or identified physiological conditions or scenarios.

The pre-processor 204 may be designed to carry out any number of processing steps for operation of system 200. In particular, the pre-processor 204 may be configured to receive physiological data obtained via input 202 and assemble the data into time-series. Additionally, the pre-processor 204 may be capable of performing steps for removing interfering and/or undesired signals associated with the data via signal rejection or filtering techniques. In some aspects, the pre-processor 204 may also be configured to assemble raw or processed signals from acquired physiological data into time-frequency representations. For instance, the pre-processor 204 may process and assemble acquired EEG data, using, for example, a multi-taper approach, to produce spectrograms, or other representations of spectral content in the data as a function of time. In some aspects, the pre-processor 204 may also be configured to receive an indication from a user and perform pre-processing steps in accordance with the indication.

In addition to the pre-processor 204, the system 200 further includes a tracking engine 206, in communication with the pre-processor 202, designed to receive pre-processed data from the pre-processor 202 and carry out steps necessary for identifying and tracking non-stationary spectral features associated with acquired physiological data, including spectral peaks. In general, the tracking engine 206 may provide time estimates for specific spectral structure present in assembled spectrograms. For instance, spectrograms commonly include multiple spectral peaks occurring substantially concurrent or simultaneously in time, and hence the tracking engine 206 may provide estimates of spectral peak features including instantaneous and time-evolutions of target parameter values, such as peak frequency, bandwidth, and amplitude. In this manner, temporal profiles of various spectral characteristics may be determined, which may then be used, in addition to other determined indicators, by the physiological state analyzer 208 to identify physiological states of a subject. For example, sleep state, or a state of consciousness, or sedation, of patient under administration of a drug with anesthetic properties, as well as confidence indications with respect to the determined state(s) may be determined by the physiological state analyzer 208. Information related to the determined state(s) may then be relayed to the output 210, along with any other desired information, in any shape or form. In some aspects, the output 210 may include a display configured to provide information or indicators with respect to time variation of non-stationary features associated with physiological data, including peak parameters, that may be formulated using graphical, spectrogram, or other representations, either intermittently or in real time.

Figure 3:
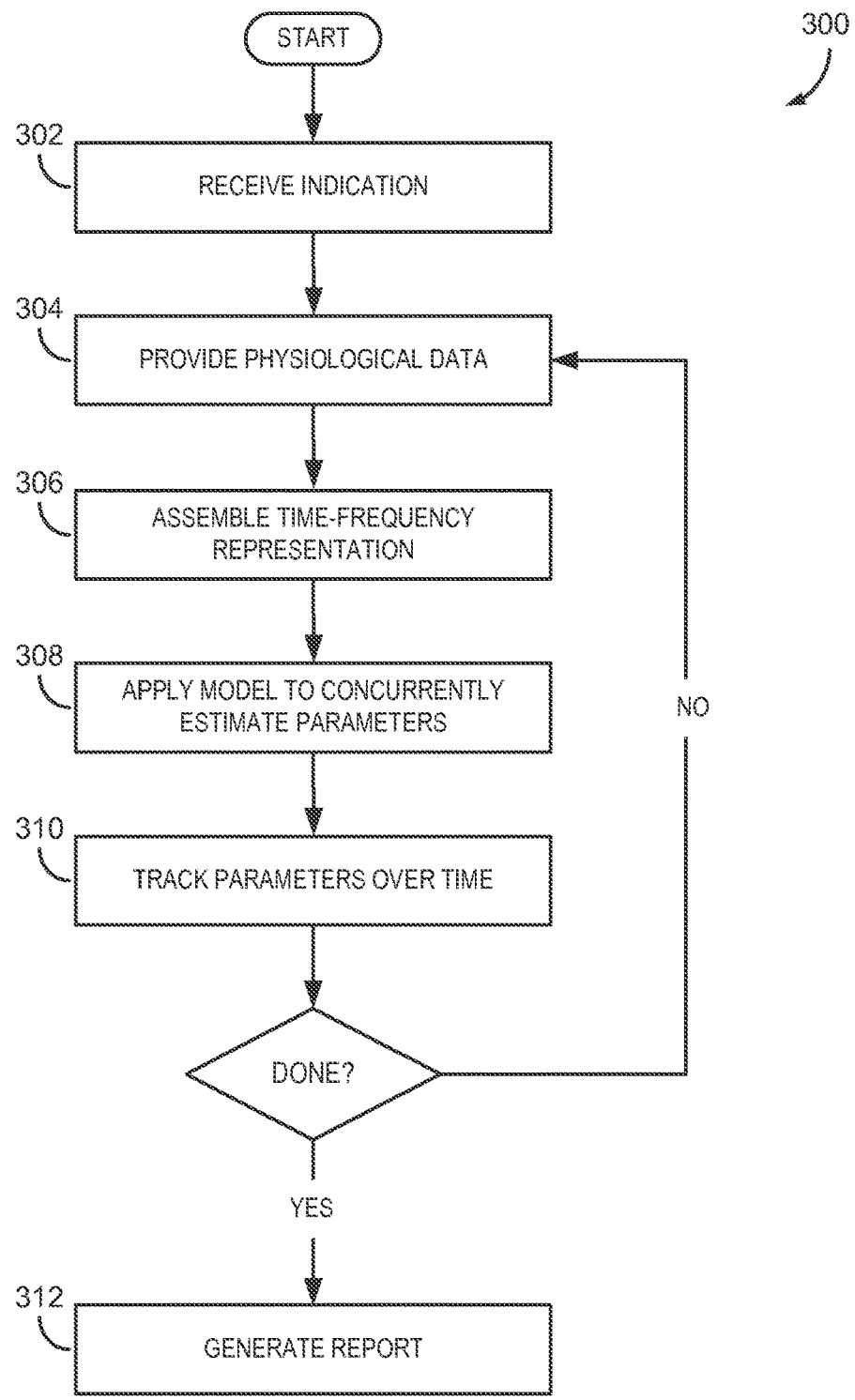
FIG. 3 is a flowchart setting forth steps for a process of tracking dynamic structure of signal data, in accordance with the present disclosure.

Turning to FIG. 3, a process 300 for tracking non-stationary spectral structure in physiological data, in accordance with the present disclosure, is illustrated. In some aspects, the process 300 may begin at process block 302 where an indication from a user, provided using systems, in accordance with the present disclosure, may be received. As described, the indication may be related to selection of specific spectral decomposition functions, to include parametric or semi-parametric functions, such as Gaussian or Gamma functions, as well as other functions, and temporal dynamic models based on physiological conditions or scenarios. In addition, at process block 302, the indication may also include selection of initial priors in relation to parameter values describing the spectral decomposition functions and temporal dynamic models. Alternatively, user-selected physiological conditions or scenarios, as well as subject characteristics, may elicit use of particular pre-programmed functions, models, priors, and other operational parameters, as described. In other aspects, pre-set configurations may be utilized with minimal user input.

At process block 304, desired amounts of physiological data may be provided. In certain aspects, a time-series of physiological data is provided and/or acquired from a subject, using, for example, systems as described. Specifically, physiological data may be acquired during a variety of clinical or experimental scenarios, such as during sleep, drug delivery, general or local anesthesia, sedation, coma, hypothermia, and so forth. Non-limiting examples of provided physiological data at process block 304 may include any combination of EEG, EMG, ECoG, LFP, ECG, EOG, GSR, $SA0_2$, OMT, or other physiological recordings, generated either independently or in a substantially concomitant fashion.

Then, at process block 304, the time-series data may be used to assemble the physiological signals into a time-frequency representation. For example, EEG data may be assembled into a spectrogram representation using a multi-taper, or other, approach, although other representations may also be possible. Subsequently, at process block 308, the dynamic model of the spectral decomposition functions may be applied using an estimation procedure that computes concurrent estimates of spectral parameters. For example, spectral parameters describing target spectral peaks, the spectral decomposition functions may be generated using a Gaussian and/or Gamma-shaped functions, which are defined using a parametric representation that characterizes a peak frequency, peak bandwidth and peak amplitude.

Since the modeling framework provided herein characterizes the number of peaks, the spectral structure of each peak, and the temporal dynamics of each peak, this estimation procedure serves identify the peaks, or other spectral features, in the data, as well as track them over time, in a substantially concomitant fashion. In this manner, at process block 310, spectral parameters describing one or more spectral features associated with physiological data, such as spectral peaks, may be tracked over time. Although, as described, Gaussian random walk models may be used to describe the temporal dynamics of the spectral parameters, other linear and non-linear models, along with other noise distributions may be used as well. In some aspects, steps associated with process blocks 304-310 may be repeated, as desired or upon fulfillment of a termination condition.

At process block 312 a report may be generated of any shape or form. For example, a graphical illustration may be provided via a display indicating a time evolution of parameters associated with one or more spectral features. Such report may be generated and/or updated in substantially real time, as new physiologically data becomes available, or may be generated after all physiological data provided has been processed, in accordance with the present disclosure. In some aspects, tracked parameters may be utilized to generate reconstructed, filtered, or denoised data using a spectrogram representation, or other representation. In other aspects, information related to tracked parameters, as well as other physiological (e.g. heart rate, behavioral response rate, sleep stage, and so on) or pharmacological (drug infusion rate, drug effect site concentration, and so on) correlates may be displayed, and/or used to provide feedback with respect to specific physiological states of a subject. In yet other aspects, such information may be used to control the state the subject, for example, by way of a continuous or intermittent control signal directed to an automated or semi-automated control system, such as a drug delivery system, or by a provided indication to a clinician.

Figure 4:
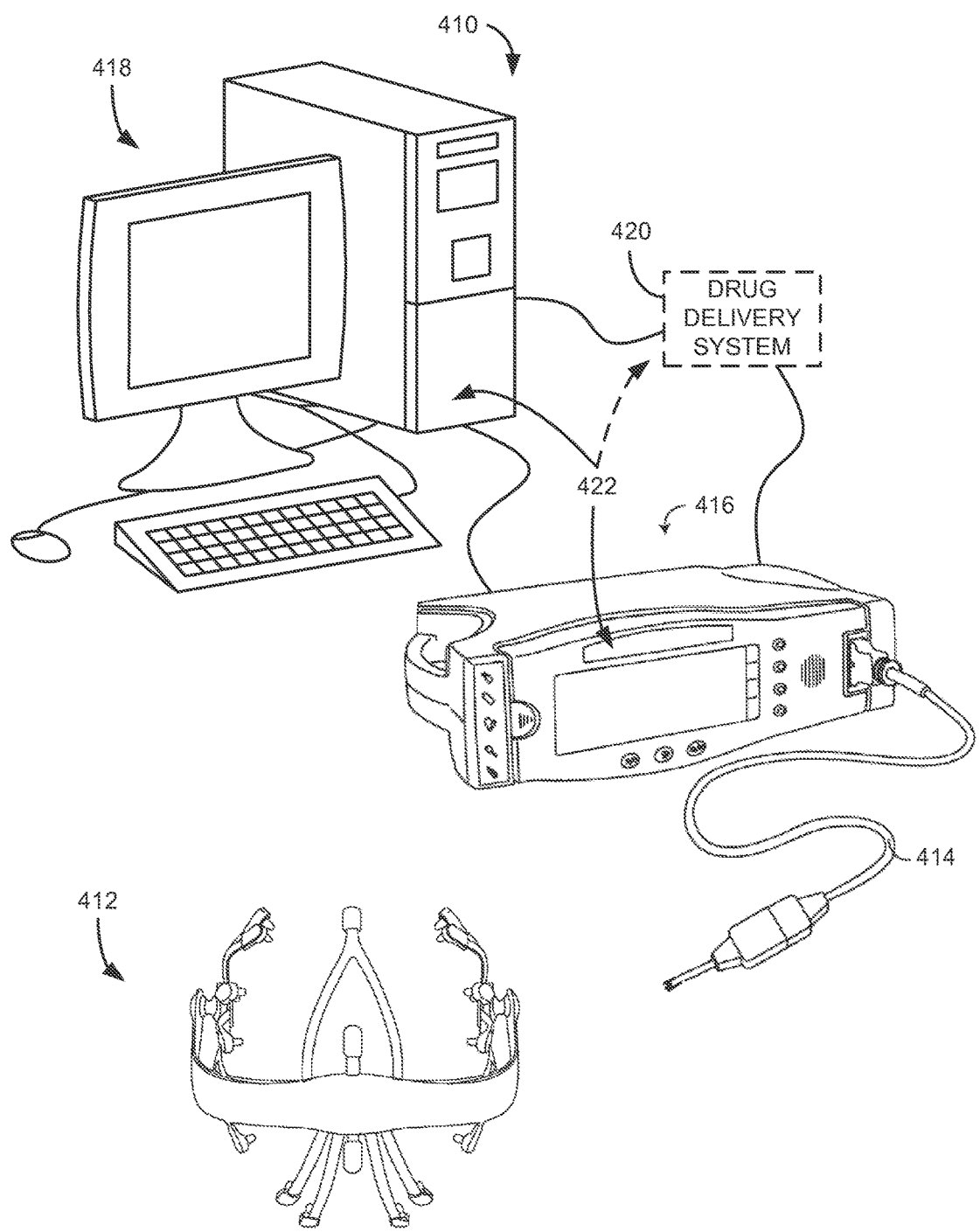
FIG. 4 is an illustration of an example monitoring and control system in accordance with the present disclosure.

Referring now to FIG. 4, a system 410 in accordance with one aspect the present invention is illustrated. The system 410 includes a patient monitoring device 412, such as a physiological monitoring device, illustrated in FIG. 4 as an EEG electrode array. However, it is contemplated that the patient monitoring device 412 may also include mechanisms for monitoring EMG, ECoG, LFP, ECG, EOG, GSR, SA0$_2$, OMT and other physiological or behavioral data.

The patient monitoring device 412 is connected via a cable 414 to communicate with a monitoring system 416. Also, the cable 414 and similar connections can be replaced by wireless connections between components. As illustrated, the monitoring system 416 may be further connected to a dedicated analysis system 418. Also, the monitoring system 416 and analysis system 418 may be integrated.

The monitoring system 416 may be configured to receive raw signals acquired by the EEG, or other physiological, electrode array, and assemble, and even display, the raw signals as waveforms. Accordingly, the analysis system 418 may receive the physiological, or other, waveforms from the monitoring system 416 and, as will be described, process the waveforms and generate a report, for example, as a printed report or, preferably, a real-time display of information. However, it is also contemplated that the functions of monitoring system 416 and analysis system 418 may be combined into a common system. In one aspect, the monitoring system 416 and analysis system 418 may be configured to determine a current and future brain state under physiologically states such as sleep, or during pharmacologically controlled conditions such as administration of anesthetic compounds, such as during general anesthesia or sedation.

In another aspect, the monitoring system 416 and analysis system 418 may be configured to characterize a patient's biological or neurophysiological state by performing a statistical test to determine which of a set of dynamic and spectral decomposition models best fits the data. For example, during sleep, predefined models relating to normal and pathological sleep could be applied to the data simultaneously. The relative likelihood of those models given the data could serve as a means of sleep pathology diagnosis. In another example, if applied to the administration of general anesthesia or sedation, the automatic identification of patient-specific dynamics could greatly improve accuracy in drug delivery or the prediction of a patient's future neural state.

The system 410 may also include a drug delivery system 420. The drug delivery system 420 may be coupled to the analysis system 418 and monitoring system 416, such that the system 410 forms a closed-loop monitoring and control system, which could be based on a control signal derived from or incorporating the time-varying model parameters. Such a closed-loop monitoring and control system in accordance with the present invention is capable of a wide range of operation, but includes user interfaces 422 to allow a user to provide input or an indication, configure the closed-loop monitoring and control system, receive feedback from the closed-loop monitoring and control system, and, if needed, reconfigure and/or override the closed-loop monitoring and control system.

In general, a monitoring and/or control system, in accordance with the present invention, is capable of creating a closed-loop control system for delivering any pharmacological and non-pharmacological agent that is correlated with the dynamic time-frequency structure of physiological data. Physiological states that may be controlled include sleep, general anesthesia, sedation, medically-induced coma, hypothermia, and so on. In one aspect of the invention, general anesthesia, sedation, or coma are controlled using a drug delivery system based on a control signal derived from the time-varying spectral decomposition function parameters estimated from physiological data. Non-limiting examples of drugs having anesthetic properties include Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, Isoflurane, Desflurane, Remifenanil, Fentanyl, Sufentanil, Alfentanil, and so on.

In some configurations, the drug delivery system 420 is not only able to control the administration of anesthetic compounds for the purpose of placing the patient in a state of reduced consciousness influenced by the anesthetic compounds, such as general anesthesia or sedation, but can also implement and reflect systems and methods for bringing a patient to and from a state of greater or lesser consciousness.

In one aspect of the present disclosure, pharmacologically-induced sleep may be controlled using the drug delivery system 420 based on a control signal derived from the time-varying spectral decomposition function parameters estimated from physiological data, as described. Non-limiting examples of drugs having properties used to aid or regulate sleep include zolpidem, eszopiclone, ramelteon, zaleplon, doxepine, benzodiazepines, antihistimines, and so on.

In another aspect of the invention, drugs administered to treat psychiatric disorders, neurocognitive disorders, or neurological disorders may be controlled using the drug delivery system 420 based on a control signal derived from the time-varying spectral decomposition function parameters estimated from physiological data.

In another aspect of the invention, drugs administered to regulate physiological variables, such as heart rate, blood pressure, respiration, or blood oxygenation, may be controlled using the drug delivery system 420 based on a control signal derived from the time-varying spectral decomposition function parameters.

Figure 5:
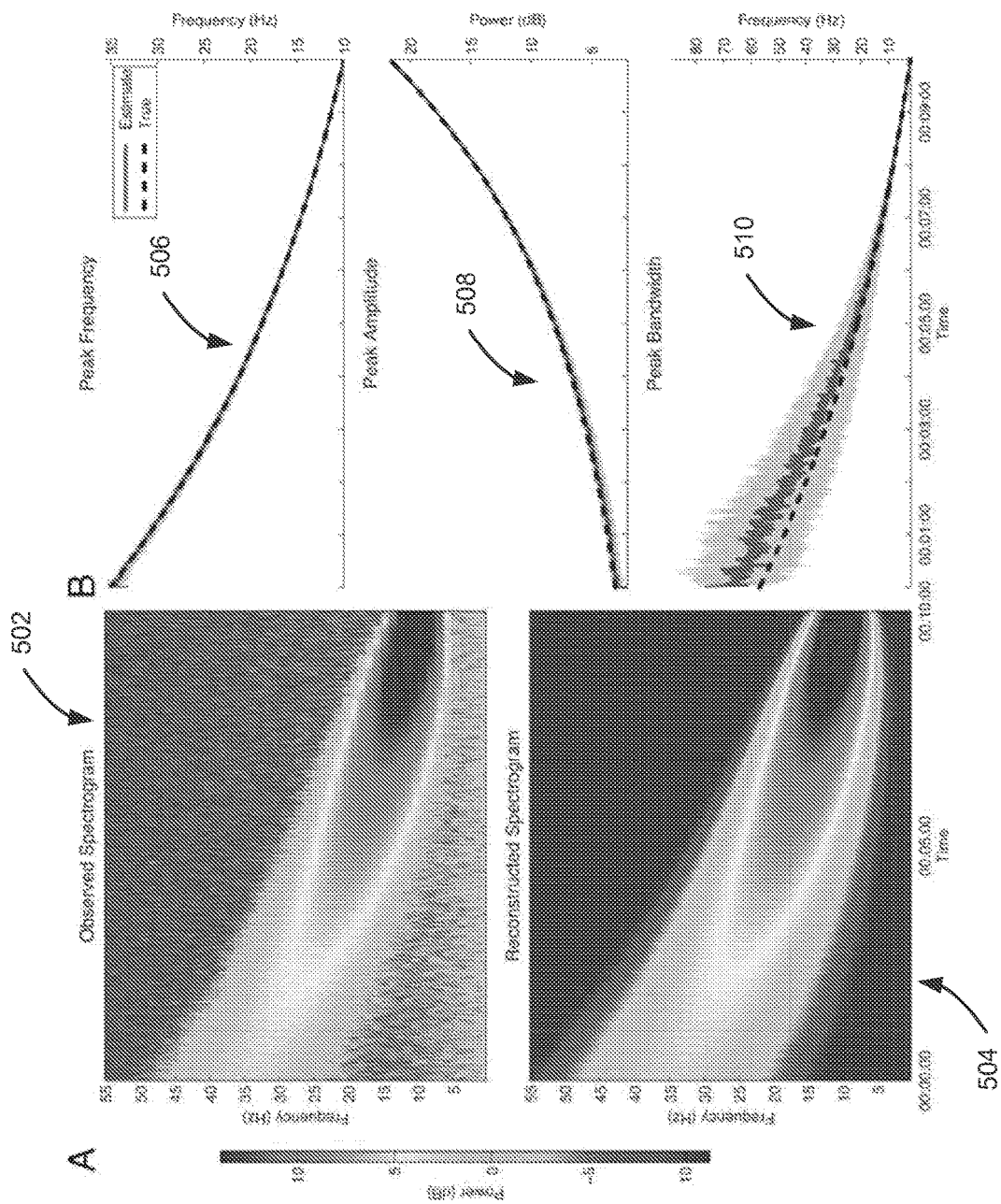
FIG. 5A is a graphical example illustrating simulated EEG data processed in accordance with the present disclosure.
FIG. 5B is a graphical illustration of the non-stationary peak parameters of FIG. 5A tracked in accordance with the present disclosure.

In another aspect of the invention, drugs administered to control pain or nociception are controlled using the drug delivery system 420 based on a control signal derived from the time-varying spectral decomposition function parameters estimated from physiological data. Non-limiting examples classes of drugs having properties used to control pain or nociception include opioids, sympatholytics such as clonidine, and NMDA receptor antagonists such as ketamine. By way of example, simulated data 502 with a chirp-like spectrum, a Gaussian bandwidth structure, and a 1/f observation noise was generated, shown in FIG. 5A. The simulation was parameterized so that:

$$F_t = \exp(m_F t + b_F)$$

$$B_t = m_B t + b_B$$

$$A_t = \exp(m_A t + b_A) \quad (15)$$

over 10 minutes time sampled at 2 Hz. The parameters $m_F$, $m_B$, $m_A$ were set to −1.2528, 2.2 and 1.9661, respectively, and $b_F$, $b_B$, $b_A$ were set ln(35), −20 and ln(0.7), respectively. Using these parameter values along with Eqn. 5, noise was added to each frequency using Eqn. 5 and $\sigma_y^2 = 1$.

As proof of concept, a bootstrap particle filter approach, in accordance with the present disclosure, was applied to simulated data 502, whereby 10,000 particles and broad uniform priors for all parameters were used. The filter output produced time varying estimates of the peak frequency 506, peak amplitude 508, and peak bandwidth 510, shown graphically in FIG. 5B. The filter estimates the peak parameters well, with the true value falling (illustrated with dashed lines) falling within the 90% confidence bounds 99.92%, 99.58%, and 97.58% of the time for the peak frequency, amplitude, and bandwidth, respectively. Consequently, the reconstructed spectrogram 504 shown in FIG. 5A strongly resembles the chirp in the original spectrogram. For the bandwidth, the estimate is initially uncertain, as the signal to noise ratio is low for the large bandwidth/low amplitude portion of the chirp. As the chirp amplitude increases and the bandwidth narrows, the bandwidth confidence bounds become increasingly tighter.

By way of another example, a high-density (64-channel) EEG data set was collected during administration of general anesthesia under the drug propofol. In this experiment, the subject was brought out and in of consciousness using a computer-controlled infusion pump, which slowly raised the concentration of propofol from a baseline of 0 mcg/ml to a peak level of 5 mcg/ml, then gradually returned the concentration back again to 0 mcg/ml. In the present example, EEG data acquired from one subject during a roughly two hour experiment was utilized, examining a single Laplacian-referenced frontal channel.

Figure 6:
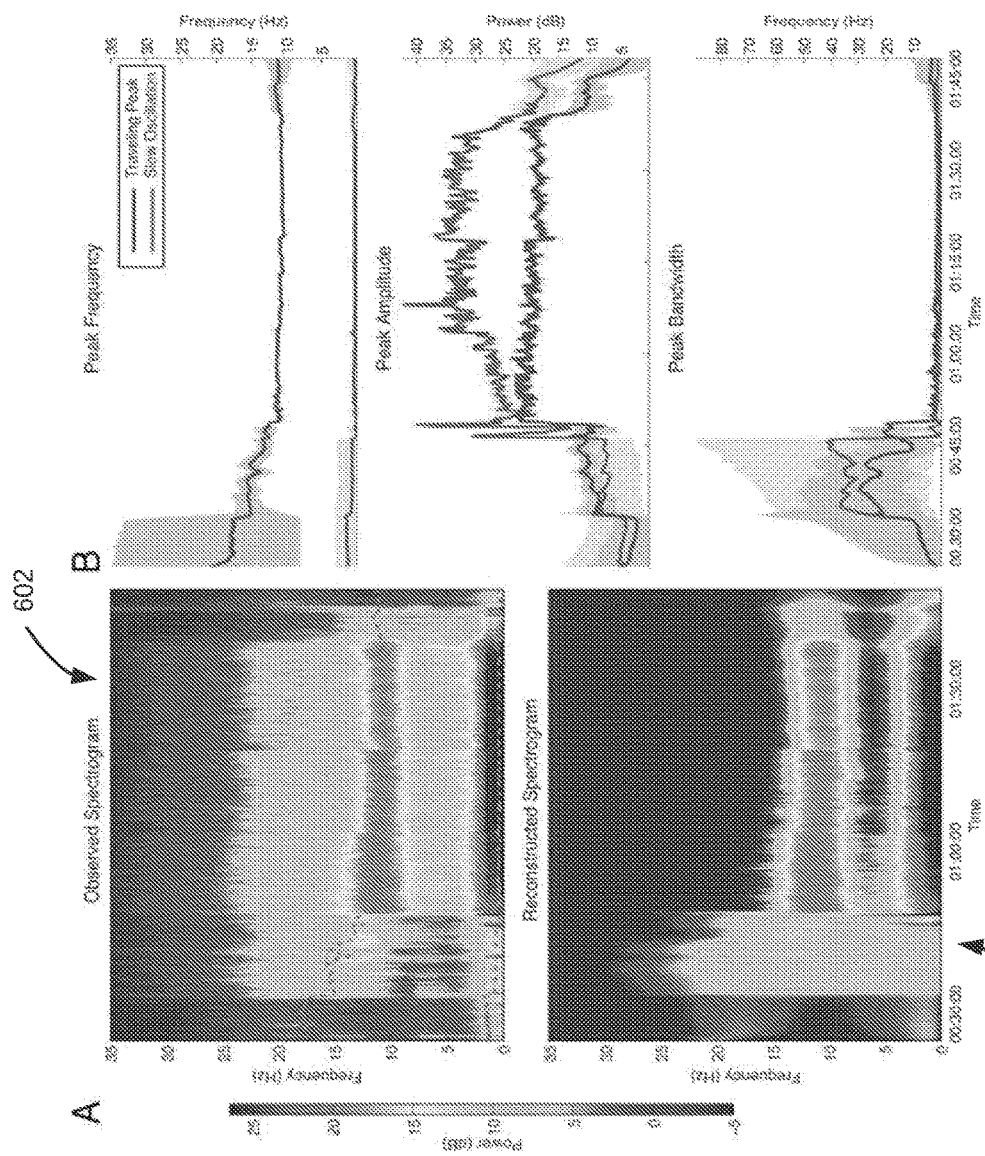
FIG. 6A is another graphical example illustrating measured EEG data processed in accordance with the present disclosure.
FIG. 6B is graphical illustration of the non-stationary peak parameters of FIG. 6A tracked in accordance with the present disclosure.

A bootstrap particle filter approach, in accordance with the present disclosure, was applied to the experimental EEG data 602, shown in FIG. 6A. Particularly, propofol data is especially suited for analysis, as described herein, as it has two major oscillatory modes that change during the administration of general anesthesia, namely, the traveling peak and the slow oscillation. The traveling peak is a rhythm that appears during light anesthesia as a broadband, low amplitude spectral peak at 15-25 Hz, then transitions to a more narrowband, high amplitude spectral peak at 8-12 Hz, as the concentration of propofol increases. The slow oscillation is a rhythm centered at less than 1.5 Hz with a highly skewed peak structure, and amplitude that greatly increases during administration of propofol. This information was used to create priors for each of the peaks.

The instantiation of the particle filter used 10000 particles to simultaneously estimate both peaks, with Gaussian and Gamma distributions used for the traveling peak and slow oscillation, respectively. Priors were chosen based on knowledge of the physiological system. Specifically, for the traveling peak, the peak frequency and bandwidth priors were uniform random between 5 and 35 Hz, and between 0 and 30 Hz, respectively. For the slow oscillation, the peak frequency and bandwidth priors were uniform random between 0 and 5 Hz, and between 0 and 3 Hz, respectively. The amplitude priors were uniform from 0 to the maximum of the long of the data power.

As in the simulation example described above, the particle filter estimates for all three peak parameters, shown in FIG. 6B, had the greatest uncertainty at the beginning and end of the experiment, when the amplitudes were lowest and the bandwidth was large. Overall, the estimates of peak frequency tracked the trends of the data peaks, for both rhythms. The Gamma structure of the slow oscillation model allowed for a reasonable reconstruction of a highly skewed spectral peak in the reconstructed spectrogram 604.

As described, the present disclosure provides a powerful tool for quantitative analysis of physiological data. Studies of relationships between estimated peak parameters and physiological correlates could provide insights into characterizing the dynamic processes governing physiological activity.

Features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system for tracking dynamic structure in physiological data, the system comprising:
   at least one input configured to receive electroencephalography ("EEG") data acquired from a subject;
   a processor configured to:
   (i) receive the EEG data from the at least one input;
   (ii) assemble a time-frequency representation of signals from the EEG data;
   (iii) generate a dynamic model of at least one non-stationary spectral peak using the time-frequency representation and a user indication;
   (iv) apply the dynamic model in a parameter estimation algorithm to compute concurrent estimates of peak parameters describing the at least one non-stationary spectral peak, the peak parameters including a peak frequency, a peak bandwidth and a peak amplitude;

(v) generate a report tracking the peak parameters of the at least one non-stationary spectral peak over time; and a display providing the report to a user.

2. The system of claim 1, wherein the time-frequency representation includes a spectrogram representation indicative of a time variation in a spectral power distribution describing the signals.

3. The system of claim 1, wherein the dynamic model characterizes dynamics of the at least one non-stationary spectral peak using at least one spectral decomposition function.

4. The system of claim 1, wherein the processor is further configured to compute a posterior probability distribution, at a time t, of the peak parameters of the at least one non-stationary spectral peak given the physiological data, the posterior probability distribution being proportional to an instantaneous likelihood.

5. The system of claim 4, wherein the processor is further configured to construct a set of particles in the parameter estimation algorithm, using the instantaneous likelihood and peak parameters.

6. The system of claim 5, wherein the processor is further configured to initialize the set of particles from a proposal density determined using information in accordance with one or both of the user indication or a physiological precedent.

7. The system of claim 5, wherein the processor is further configured to sample a new value for each of the set of particles at a time t in accordance with a prediction density.

8. The system of claim 5, wherein the processor is further configured to resample the set of particles according to normalized weights computed using the instantaneous likelihood.

9. The system of claim 5, wherein an estimate of peak parameters at a time t is defined as a component-wise median of the set of particles.

10. The system of claim 5, wherein the processor is further configured to determine confidence values for the peak parameters by computing component-wise percentile values of the set of particles using a predetermined significance.

11. The system of claim 1, wherein the report is indicative of a physiological state of the subject using the tracked peak parameters.

12. A method for tracking dynamic structure in physiological data comprising:

providing electroencephalogram ("EEG") data acquired from a subject using a plurality of EEG sensors;

using at least one processor configured for:
assembling a time-frequency representation of signals from the EEG data;
generating a dynamic model of at least one non-stationary spectral peak using the time-frequency representation and a user indication;
applying the dynamic model of at least one non-stationary spectral peak in a parameter estimation algorithm to compute concurrent estimates of peak parameters describing the at least one non-stationary spectral peak, the peak parameters including a peak frequency, a peak bandwidth and a peak amplitude;
generating a report tracking the peak parameters of the at least one non-stationary spectral peak over time; and
providing the report to a user.

13. The method of claim 12, wherein the time-frequency representation includes a spectrogram representation indicative of a time variation in a spectral power distribution describing the signals.

14. The method of claim 12, wherein the dynamic model characterizes dynamics of the at least one non-stationary spectral peak using at least one spectral decomposition function.

15. The method of claim 13, further comprising computing a posterior probability distribution, at a time t, of the peak parameters of the at least one non-stationary spectral peak given the physiological data, the posterior probability distribution being proportional to an instantaneous likelihood.

16. The method of claim 15, further comprising constructing a set of particles in the parameter estimation algorithm, using the instantaneous likelihood and peak parameters.

17. The method of claim 16 further comprising initializing the set of particles from a proposal density determined using information in accordance with one or both of the user indication or a physiological precedent.

18. The method of claim 16 further comprising sampling a new value for each of the set of particles at a time t in accordance with a prediction density.

19. The method of claim 16 further comprising resampling the set of particles according to normalized weights computed using the instantaneous likelihood.

20. The method of claim 16, wherein an estimate of peak parameters at a time t is defined as a component-wise median of the set of particles.

21. The method of claim 16 further comprising determining confidence values for the peak parameters by computing component-wise percentile values of the set of particles using a predetermined significance.

22. The method of claim 12, further comprising acquiring the time-series of EEG data using at least one sensor coupled to the subject experiencing an administration of at least one drug having anesthetic properties, a psychiatric condition, a neurological condition, sleep, or any combination thereof.

23. The method of claim 12, wherein the report is indicative of a physiological state of the subject using the tracked peak parameters.

24. A system for tracking dynamic structure in physiological data, the system comprising:

at least one input configured to receive physiological data acquired from a subject;

a processor configured to:
(i) receive the physiological data from the at least one input;
(ii) assemble a time-frequency representation of signals from the physiological data;
(iii) generate a dynamic model of at least one non-stationary spectral feature using the time-frequency representation and a user indication;
(iv) apply the dynamic model in a parameter estimation algorithm to compute concurrent estimates of spectral parameters describing the at least one non-stationary spectral feature;
(v) generate a report tracking the spectral parameters of the at least one non-stationary spectral feature over time; and
(vi) communicate the report to one of a user via a display or to a drug delivery system to control operation of the drug delivery system.

25. The system of claim 24, wherein the physiological data includes electroencephalography ("EEG") data.

26. The system of claim 24, wherein the time-frequency representation includes a spectrogram representation indicative of a time variation in a spectral power distribution describing the signals.

27. The system of claim 24, wherein the dynamic model characterizes dynamics of the at least one non-stationary spectral feature using at least one spectral decomposition function.

28. The system of claim 24, wherein the processor is further configured to compute a posterior probability distribution, at a time t, of the peak parameters of the at least one non-stationary spectral peak given the physiological data, the posterior probability distribution being proportional to an instantaneous likelihood.

29. The system of claim 24, wherein the processor is further configured to apply a statistical sampling technique, a Kalman filtering technique, a variational Bayes estimator technique, and an Expectation-Maximization ("EM") technique in the parameter estimation algorithm.

30. The system of claim 24, wherein the processor is further configured to initialize parameter values from a proposal density determined using information in accordance with one or both of the user indication or a physiological precedent.

31. The system of claim 24, wherein the spectral parameters include a peak frequency, a peak bandwidth and a peak amplitude.

32. The system of claim 24, wherein the processor is further configured to determine confidence values for the spectral parameters.

33. The system of claim 24, wherein the processor is further configured to generate multiple dynamic models related to dynamic features of the physiological data, and compare the dynamic models using a relative goodness-of-fit indicator.

34. The system of claim 24, wherein the processor is further generate the dynamic model using information related to physiological correlates including a drug level, a drug concentration, and a behavior, or any combination thereof.

35. The system of claim 24, wherein the report is indicative of a physiological state of the subject using the tracked spectral parameters.

* * * * *